(12) United States Patent
Grier

(10) Patent No.: US 7,233,423 B2
(45) Date of Patent: Jun. 19, 2007

(54) OPTICAL FRACTIONATION METHODS AND APPARATUS

(75) Inventor: David G. Grier, New York, NY (US)

(73) Assignee: University of Chicago, Chicago, IL (US)

( * ) Notice: Subject to any disclaimer, the term of this patent is extended or adjusted under 35 U.S.C. 154(b) by 119 days.

(21) Appl. No.: 10/845,758

(22) Filed: May 14, 2004

(65) Prior Publication Data
US 2005/0078343 A1    Apr. 14, 2005

Related U.S. Application Data

(60) Provisional application No. 60/498,868, filed on Aug. 29, 2003, provisional application No. 60/471,149, filed on May 16, 2003.

(51) Int. Cl.
G02B 5/32 (2006.01)
G02B 1/00 (2006.01)
G02B 5/18 (2006.01)
G02B 27/44 (2006.01)

(52) U.S. Cl. .......................... 359/15; 359/15; 359/566; 359/900

(58) Field of Classification Search ............ 359/15–19, 359/566, 569; 349/201
See application file for complete search history.

(56) References Cited

U.S. PATENT DOCUMENTS

| | | | |
|---|---|---|---|
| 6,055,106 A | 4/2000 | Grier et al. | |
| 6,624,940 B1 | 9/2003 | Grier et al. | |
| 6,815,664 B2 | 11/2004 | Wang et al. | |
| 2003/0007894 A1 | 1/2003 | Wang et al. | |
| 2003/0086175 A1 | 5/2003 | Grier et al. | |
| 2005/0061962 A1* | 3/2005 | Mueth et al. ............... | 250/251 |
| 2005/0094232 A1 | 5/2005 | Kibar | |
| 2005/0152039 A1* | 7/2005 | Grier et al. ................. | 359/614 |
| 2005/0164372 A1 | 7/2005 | Kibar | |
| 2005/0207940 A1* | 9/2005 | Butler et al. .................. | 422/73 |
| 2005/0221333 A1* | 10/2005 | Sundarajan et al. ........... | 435/6 |

OTHER PUBLICATIONS

N. R. Heckenberg et al., "Laser Beams with Phase Singularities" Opt. & uant. Elect., vol. 24, S951 (1992).

H He, NR Heckenberg, and H. Rubinsztein-Dunlop, "Optical particle trapping with higher-order" J Mod Optics 42, 217-233 (1995).

H He, MEJ Friese, NR Heckenberg, and H Rubinsztein-Dunlop, "Direct Observation of Transfer of Angular Momentum to Absorptive Particles from a Laser Beam with Phase Singularity" Phys Rev Let 75 826-829 (1995) (and references therein).

(Continued)

Primary Examiner—Fayez G. Assaf
(74) Attorney, Agent, or Firm—Foley & Lardner LLP

(57) ABSTRACT

Static arrays of optical traps can be used to sort microscopic objects with exponential sensitivity to size. Such optical fractionation relies on competition between an externally applied force and the moving objects' differing affinities for optical gradient traps. In a reverse fractionation method, objects that are more strongly influenced by the traps tend to become kinetically locked in to the array and are systematically deflected back into an input flow. In a thermal ratcheting method, patterns are spaced to allow particle diffusion, thus providing the opportunity for forward or reverse movement through the patterns. Unlike other sorting techniques, optical fractionation can operate continuously and can be continuously optimized. The exponential sensitivity arises quite generally from the particle size dependence of the potential wells' apparent widths.

15 Claims, 7 Drawing Sheets

OTHER PUBLICATIONS

MEJ Friese, J Enger, H Rubinsztein-Dunlop and NR Heckebber, "Optical Angular-Momentum Transfer to Trapped Absorbing Particles" Phys Rev A 54 1593-1596 (1996).

KT Gahagan and GA Swartlander, "Optical Vortex Trapping of Particles" Optics Letters 21 827-829 (1996).

KT Gahagan and GA Swartlander "Trapping of Low-Index Microparticles in an Optical Vortex" J Opt Soc Am B-15 524-534 (1998).

D'Henlon et al, "Measurement of the Optical Force and Trapping Range of a Single Beam Gradient Optical Trap for Micron-Sized Latex Spheres." J Modern Optics 595-601 (1994).

H. Dammann and K. Gortler, "High-Efficiency In-Line Multiple Imaging by Means of Multiple Phase Holograms" Optics Comm 3 312-318 (1971).

M.P. Dames, R.J. Dowling, P. McKee and D. Wood "Efficient Optical Elements to Generate Intensity Weighted Spot Arrays: Design and Fabrication." 30 2685 (1991).

SE Broonfield et al, "Programmable Binary Phase-only Optical Device based on Felloelectric Liquid Crystal SLM" Electronics Letters 28 26-28.

J. Gourlay, S. Samus et al, "Real-Time Binary Phase Holograms on a Reflective Feroelectric Liquid-Crystal Spatial Light Modulator" Applied Optics 33 8521-8254 (1994).

* cited by examiner

OPTICAL FRACTIONATION METHODS AND APPARATUS

This invention was made with U.S. Government support under Grants No. DMR-0304960 and DBI-0233971 awarded by the National Science Foundation, and through the MRSEC Program of the National Science Foundation under Award No. DMR-0213745. The U.S. Government also has certain rights to the invention pursuant to these contracts and awards.

FIELD OF THE INVENTION

This invention is concerned generally with implementation of a method and system for sorting small particles. More particularly, the invention is directed to use of holographic optical tweezer technique that sorts small objects such as macromolecules, biomolecules, nanoclusters, colloidal particles and biological cells.

BACKGROUND OF THE INVENTION

Optical tweezers use optical gradient forces to trap small, usually micrometer-scale, volumes of matter in both two and three dimensions. A holographic form of optical tweezer can use a computer-generated diffractive optical element to create large numbers of optical tweezers from a single laser beam. These tweezers can be arranged in any desired configuration dependent on the need at hand.

Although systems are known to move particles precisely and with a relatively high degree of confidence, conventional systems require a separate hologram to be projected for each discrete step of a particle's motion. Computing multiple holograms can be time consuming and requires substantial computational effort. Furthermore, computer-addressable projection systems required to implement such computer-generated optical tweezers or other dynamic optical tweezer systems, such as scanned optical tweezers, tend to be prohibitively expensive.

SUMMARY OF THE INVENTION

The behavior of many technologically and commercially important systems results from classical transport through modulated potential energy landscapes. One method of utilizing these behaviors is optical fractionation. Optical fractionation can continuously (within a given time segment) sort populations of small objects into separate fractions on the basis of their differing abilities to move through arrays of optical traps. In particular, objects driven by an external force, such as viscous drag in a flowing fluid, encounter an array of traps whose axes of symmetry are oriented at an angle with respect to the driving force. Typically, these traps would be created with the holographic optical tweezer technique. Those objects more strongly influenced by the potential energy wells created by the traps tend to hop from trap to trap, and so are deflected away from the direction of the driving force. Other objects that are more strongly influenced by the driving force or less strongly influenced by the optical traps pass through the array undeflected. Depending on the configuration of the traps, the present invention may be utilized to deflect different fractions by different amounts. In some circumstances, the clean separation of the above described binary embodiment is preferred. However, it is within the scope of the invention to choose multiple fractions for collection. For example, in one embodiment, a heterogeneous sample may be fanned out in a continous range of directions in an "optical chromatography" method. The deflected and undeflected fractions can be collected separately.

Typically, the heterogeneous input sample and the output fractions are dispersed in a fluid flowing through channels. In one preferred embodiment, the channels take the form of a so-called H-junction, in which two inputs, one containing the input mixed sample and the other containing just the background fluid, are brought together to flow side-by-side for a set distance before being separated into two output channels. If the channels are small enough, the Reynolds number for the flowing fluid is small enough that the two flows do not mix, but rather flow side-by-side in a laminar manner. Consequently, objects in the input flow would not ordinarily cross the separatrix between the flows into the buffer channel, except perhaps by diffusion.

One aspect of the present invention relates to optical fractionation using an array of discrete optical traps to continuously sort small objects on the basis of their relative affinities for the optical traps and for a competing externally applied force. The undesired fraction is more diffusive or motile than the desired fraction. However, another aspect of the present invention relates to "reverse" optical fractionation. In reverse optical fractionation, the desired fraction is more diffusive or motile than the undesired fraction.

Another aspect of the present invention involves a modification of a technique known as optical peristalsis, in which small objects are transported deterministically by a projected sequence of optical trapping patterns. The difference between optical peristalsis and the disclosed optical thermal ratchet technique endows the system and method with qualitatively new capabilities, including without limitation bidirectional pumping through an effect known as flux reversal and also embodies new possibilities for sorting heterogeneous samples.

BRIEF DESCRIPTION OF THE DRAWINGS

FIG. 4A depicts representative trajectories of 0.79 micrometer radius spheres measured at 1/60 sec. intervals; FIG. 4B shows the trajectories of 0.5 micrometer radius spheres obtained simultaneously; FIG. 4C is the time-averaged areal density of 0.79 micrometer radius spheres relative to their mean areal density; and FIG. 4D is time-averaged areal density of 0.50 micrometer radius diameter spheres relative to their mean areal density.

DETAILED DESCRIPTION OF PREFERRED EMBODIMENTS

Figure 1:
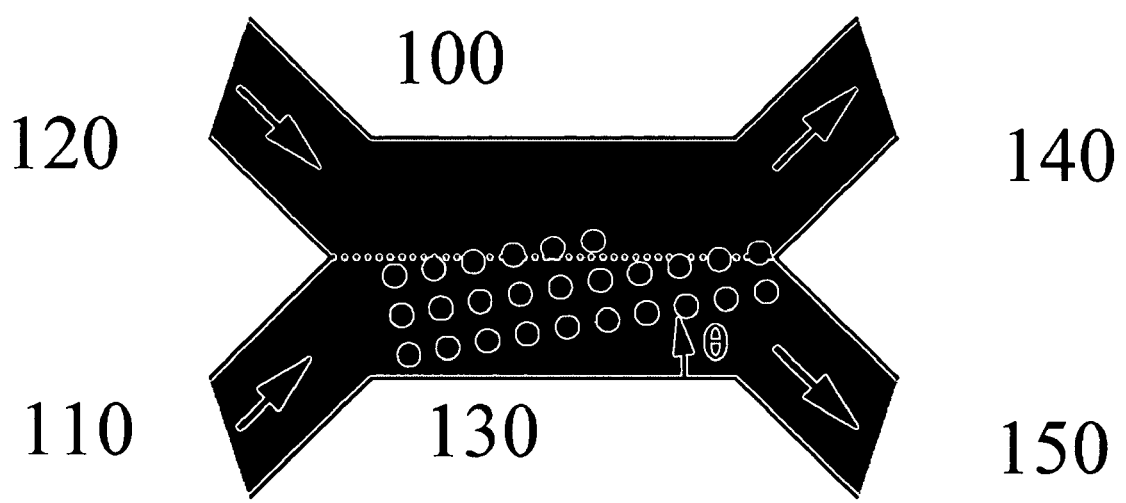
FIG. 1 shows optical fractionation wherein a microfluidic H-junction comprises a first flow containing the heterogeneous sample to be fractionated and a second flow composed of the background, or buffer fluid.

The present invention relates to methods and apparatus for optical fractionation. One aspect relates to optical fractionation using an array of discrete optical traps to continuously sort small objects on the basis of their relative affinities for the optical traps and for a competing externally applied force. Another aspect of the present invention relates to "reverse" optical fractionation. A third aspect of the present invention relates to the use of a "ratcheting" optical fractionation technique.

A model system has been developed for studying modulated transport, in which individual colloidal spheres are driven through a regular array of potential wells created with discrete optical tweezers, while their motions are analyzed with digital video microscopy. Experiments on this system demonstrate that driven particles trace out a Devil's staircase hierarchy of kinetically locked-in states as the array is rotated with respect to the driving force. Within each of these states, the particles' trajectories follow symmetry-selected directions through the lattice of traps independent of the array's orientation and therefore are deflected laterally away from the driving force. Such deflection was predicted to provide the basis for a continuous fractionation technique in which the selected population is deflected by an array of traps while the rest of the sample passes through unhindered. This methodology presents a practical demonstration of optical fractionation and furthermore demonstrates that optical fractionation's resolution can depend exponentially on particle size. Therefore this methodology offers sensitivity unparalleled by any previously reported sorting technique.

One can demonstrate one form of the concept of optical fractionation by using an array of discrete optical traps to continuously sort small objects on the basis of their relative affinities for the optical traps and for a competing externally applied force. This approach utilizes trajectories of two different sizes of colloidal silica spheres dispersed in water flowing past a linear array of optical tweezers arranged at an angle with respect to the flow. The flowing colloidal dispersion was confined to a 4 mm×0.7 mm×40 µm glass channel formed by bonding the edges of a cover slip to a microscopic slide. A pressure difference applied across this channel creates a roughly constant Poisseuille flow of about 60 µm/sec over several minutes. The sample consisted of a mixture of a=0.79 µm radius spheres (Duke Scientific Duke Scientific Corporation, 2463 Faber Place Palo Alto, Calif. 94303, Lot No. 24169) and α=0.5 µm radius spheres (Duke Scientific Lot No. 19057), both of which can be tracked to within 30 nm in the plane at 1/60 sec intervals using conventional bright-field microscopy and digital video analysis. Furthermore, these spheres can be reliably distinguished on the basis of their appearance, and thus provide an ideal model system whose microscopic response to optical fractionation can be monitored in real time. Typical trajectories for large and small spheres appear in FIGS. 4A and 4B, respectively.

Silica spheres are roughly twice as dense as water and therefore settle into a monolayer just above the lower glass wall of the channel, with the smaller spheres floating somewhat higher because they are lighter. Given the Poisseuille flow profile within the channel, the smaller spheres travel somewhat faster, with a mean speed of $u_s = 17 \pm 9$ µm/sec, compared with the larger spheres' $u_b = 13 \pm 2$ µm/sec. The viscous drag on a stationary sphere, $F_1 = \gamma u$, is characterized by a drag coefficient, $\gamma$, that depends both on the sphere's radius, $\alpha$, and also on its proximity to bounding surfaces. The populations' drag coefficients can be estimated from their diffusivities, D, using the Einstein-Smoluchowsky relation $D = k_B T/\gamma$, where $K_B T$ is the thermal energy scale at temperature T. The diffusivities, in turn, can be measured from the transverse velocity fluctuations in trajectories such as those in FIGS. 4A and 4B. More generally, the applied force $F_1$ can be provided by processes such as electrophoresis, electroosmosis, magnetophoresis, or gravitational sedimentation.

The optical traps for this illustration were created with the dynamic holographic optical tweezer technique. Twelve discrete optical tweezers, each powered by 1.7±0.8 mW of laser light at 532 nm, were arranged in a line at $\theta = 12.0° \pm 0.5°$ with respect to the channel's axis, with center-to-center spacing of b=3.6±0.1 µ/m. Each trap may be modeled as a roughly Gaussian potential well whose depth, $V_o$, and width, $\sigma$, both depend on the sphere's radius, $\alpha$.

Were it not for the optical traps, a particle driven through a viscous fluid by an applied force $F_1$ would travel at a mean speed $u = F_1/\gamma$ Provided that the applied force $F_1$ is sufficiently large, the optical traps only deflect a particle away from its trajectory. If the deflection is small, then the particle will continue to travel downstream from the line of traps and may be said to have escaped from the line of traps. On the other hand, each trap can be strong enough to deflect the particle into its neighbor's domain of influence. In this case, the particle will be passed from trap to trap and is effectively captured by the array. This is the mechanism of kinetically locked-in transport. The deflection angle $\theta$ was selected to be close to the angle of maximum deflection for this locked-in transport. The relative deflection of captured particles' trajectories relative to escaped particles' trajectories is the basis for sorting by optical fractionation. The deflected and undeflected fractions can be collected separately and this process is shown schematically in FIG. 1.

Given the traps' geometry, the laser power was set between the empirically determined thresholds for escape of the large and small spheres. The trajectories in FIGS. 4A and 4B demonstrate that the larger spheres are systematically deflected by the array of traps under these conditions, while the smaller spheres are not. Consequently, small spheres flow unimpeded into the resulting shadow in the distribution of large spheres, where they can be collected. Conversely, the deflected large spheres are concentrated into a small region at the end of the optical trap array where they may be separately collected. Because the purification of small spheres and the concentration of large spheres results from lateral deflection of the larger fraction, this optical fractionation process can proceed continuously and thus offers advantages over batch-mode techniques such as gel electrophoresis.

Figure 4:
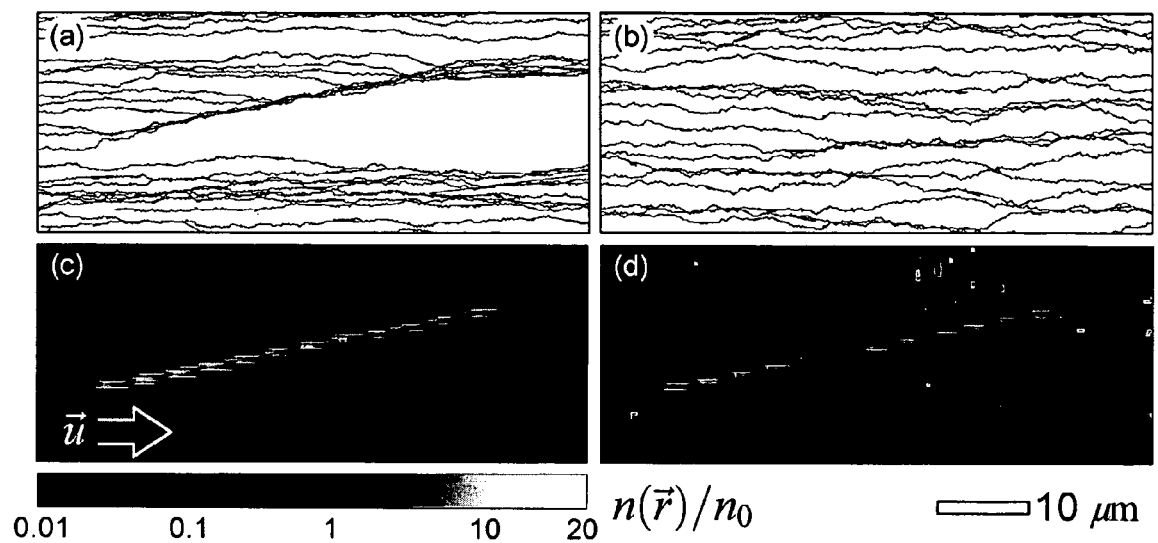
FIG. 4 shows the optical separation of large silica sphere from small silica spheres.

This qualitative interpretation of just a few trajectories can be made more compelling by considering the statistics of tens of thousands of trajectories collected in FIGS. 4C and 4D. Here, we plot the time-averaged areal density $n(\vec{r})$ of spheres in regions of area 60×24 µm² centered at $\vec{r}$, normalized by the mean time-averaged areal denisity no for each population. The spheres' relative affinities for the traps can be gauged in that large spheres are roughly eighteen times more likely to be found in a trap than in the bulk flow, while small spheres are only three times more likely. Given the spheres' relative speeds, these ratios are consistent with the larger spheres being temporarily stopped in local potential minima while the smaller spheres are simply slowed.

The quality of the resulting separation can be gauged by measuring the relative population concentrations as a function of position in the flow:

$$Q(\vec{r}) = \frac{n_b(\vec{r}) - n_s(\vec{r})}{n_b(\vec{r}) + n_s(\vec{r})} \quad (1)$$

Figure 5:
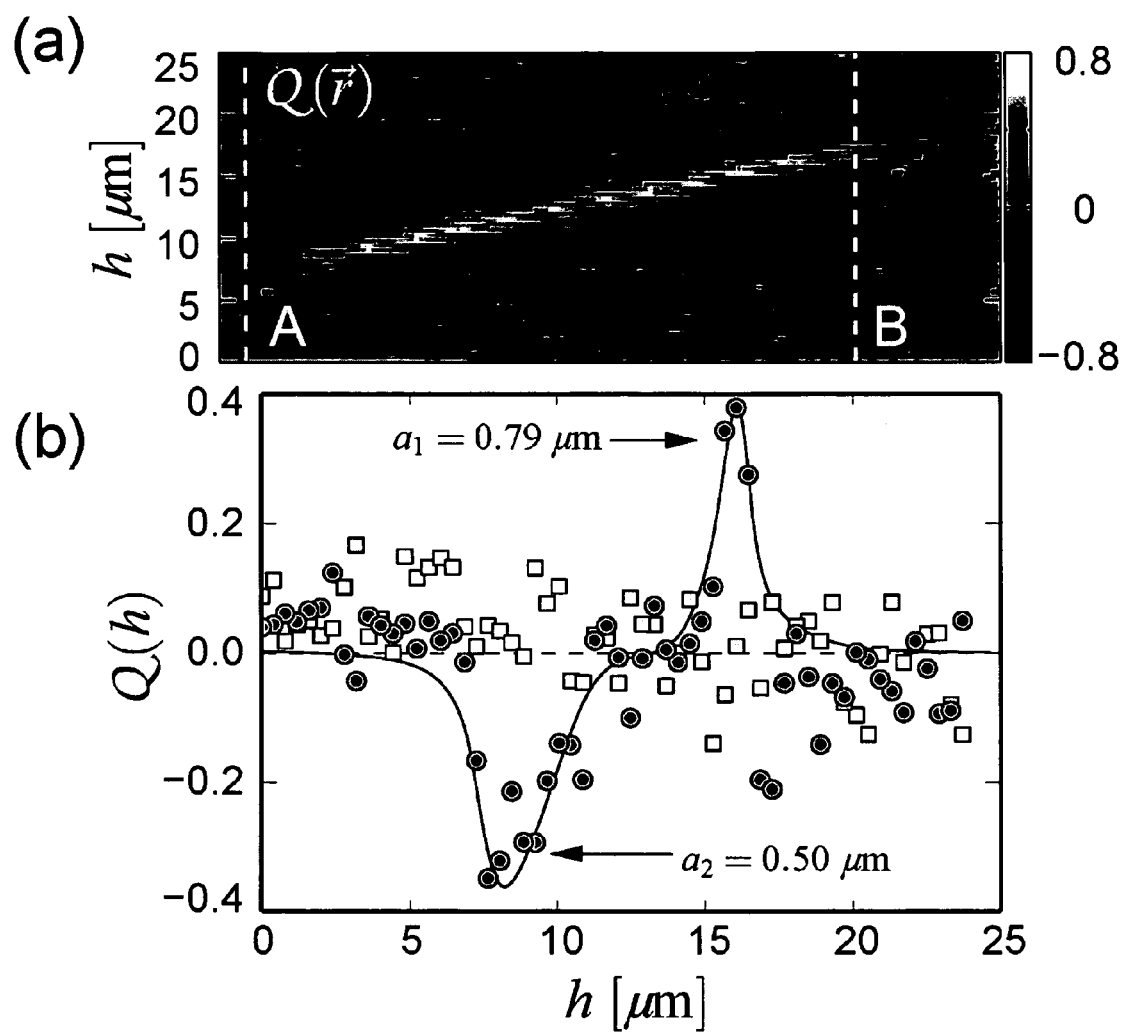
FIG. 5 illustrates the spatially resolved quality of separation obtained with a single line of optical traps.

This figure of merit, shown in FIGS. 5A and 5B, reaches a maximum value of unity in a region containing only large spheres, and minus one in a region with only small spheres. A section transverse to the flow along the line A in FIG. 5A before the array of traps reveals a perfectly mixed sample, Q(y)=0, as shown by the small circles in FIG. 5B. A similar section after the array of traps, along line B, and plotted as larger circles in FIG. 5B, demonstrates roughly 40 percent purification of both large and small spheres. Much of the background can be attributed to collisions in the array of traps that allowed large spheres to escape. Collision-induced escape is evident in the large spheres' concentration profile downstream of the trap array in FIG. 4C, with collisions and escape becoming increasingly likely as the large spheres saturate the downstream end of the trap array. Such collisions are most effectively avoided by projecting several parallel lines of traps. As few as three lines provide essentially perfect fractionation under the present experimental conditions, with more becoming necessary in denser suspensions.

The data in FIGS. 4A, 4B and 5A, 5B demonstrate that arrays of discrete optical traps can continuously separate spheres on the basis of their size. Considering the physical conditions leading one type of particle to escape from an array of traps while another type is captured provides the basis for optimizing optical fractionation.

For simplicity, the influence of just two discrete optical traps was analyzed, centered at $x=\pm b/2$, on a particle near their midpoint at $x=0$. The particle's total potential energy is $$V(\vec{r}) = -V_0 \left[ \exp\left(-\frac{\left(x-\frac{b}{2}\right)^2}{2\sigma^2}\right) + \exp\left(-\frac{\left(x+\frac{b}{2}\right)^2}{2\sigma^2}\right) \right] \exp\left(-\frac{y^2}{2\sigma^2}\right) - \vec{F}_1 \cdot \vec{r} \quad (2)$$

It escapes by passing through a point where $$F_y(\vec{r}) = F_1 \sin\theta - \frac{V_0}{\sigma^2} y \left[ \exp\left(-\frac{\left(x-\frac{b}{2}\right)^2}{2\sigma^2}\right) + \exp\left(-\frac{\left(x+\frac{b}{2}\right)^2}{2\sigma^2}\right) \right] \exp\left(-\frac{y^2}{2\sigma^2}\right) \quad (3)$$

$$= 0$$

the y component of the total force, vanishes. Particles should escape most readily near $x=0$, where the trapping force is weakest, and $y=\sigma$ the separation at of maximum force. In this case, the maximum attainable deflection still admitting captured trajectories is given by $$\sin\theta \approx f(a)\exp\left(-\frac{b^2}{8\zeta^2}\right) \quad (4)$$

where the relative trap strength $f(\alpha)=(2/\sqrt{e})V_0/V_1$ depends on particles' material properties, including their size, but not on the configuration of the traps. Here $V_1=F_1\sigma$ characterizes the driving force. Similarly, the apparent extent $\sigma(a)$ of an optical trap depends not only on the width $\sigma_o$ of the focused beam of light, but also on the size of the particle:

$$\sigma^2(a) \approx \sigma_o^2 + a^2 \quad (5)$$

Larger particles are influenced by the optical trap at a larger range than smaller particles. This qualitative dependence of $\sigma$ on a established conditions for exponentially sensitive separations. We will continue to use Eq. (5) for illustrative example purposes.

For the present data $V_0/V_1=1.3$ and 0.73 were obtained for the large and small spheres, respectively, using thermal fluctuation analysis to characterize the optical traps' depths. The same analysis reveals $\sigma=0.94\pm0.07$ µm and $0.74\pm0.07$ µm for the traps' apparent widths. These results suggest critical angles of $\theta=14°\pm1°$ for the large spheres and $\theta=3°\pm2°$ for the small, which is consistent with the observation that large spheres are systemically captured, while small spheres escape. The total lateral deflection for a marginally captured particle in an N-trap array is $(N-1)b \sin\theta$. Accordingly, $$\Delta(a|b) = b \sin\theta \quad (6)$$

establishes the lateral deflection per trap, and thus characterizes the array's efficiency. Choosing the inter-trap spacing $b=2\sigma(\alpha)$ optimizes this efficiency at $\Delta=4/e\, V_0/F_1$. This result is useful for designing a practical optical fractionation system, but does not necessarily optimize its sensitivity to particle size.

The sensitivity may be formulated as $$S(a|b) \equiv \frac{\partial \Delta(a|b)}{\partial a}, \quad (7)$$

and is optimized by setting $$\frac{\partial S(a|b)}{\partial b} = \frac{\partial^2 \Delta(a|b)}{\partial b \partial a} = 0 \quad (8)$$

This yields $$\frac{b^2}{2(\sigma_0^2 + a^2)} = 3 - \chi(a) + \sqrt{9 - 2\chi(a) + \chi^2(a)}, \quad (9)$$

where $$\chi(a) = \frac{a^2 + \sigma_0^2}{a} \frac{f'(a)}{f(a)} \quad (10)$$

Equation (9) establishes the spacing between traps b for which an array of optical traps at angle θ will most sensitively distinguish between "large" particles, which will be captured, and "small" particles, which will escape.

As a practical example, these results may be applied to optimizing optical fractionation in a viscous flow. For particles comparable in size to the wavelength of light, or smaller, the depth of the potential well should scale with the particles' volume $V_0 = A\alpha^3$, while the viscous drag force is proportional to their radius, $V_1 = B\alpha$, so that $f(\alpha)$ is proportional to $\alpha^2$. Substituting the optimized spacing b into the criterion for flow-based separation in Eq. (4) yields $$\sin\theta \approx \frac{2A a^2}{B} \exp\left(\frac{\sigma_0^2}{2a^2} - \frac{3}{4} - \frac{1}{2}\sqrt{\frac{9}{4} + \frac{\sigma_0^2}{a^2} + \frac{\sigma_0^2}{a^4}}\right). \quad (11)$$

Equations (4) and (5) further demonstrate that optical fractionation depends only linearly on the depths of the potential wells. Thus, variations in potential well depths for practical arrays of optical vortices should degrade the separation's resolution only linearly, and generally can be compensated for by the substantially stronger dependence on particle size.

In summary, the foregoing examples have demonstrated optical fractionation in practice for a model system of colloidal silica spheres, and have shown that the technique promises exponential sensitivity for size-based separations. The foregoing considerations demonstrate that an optical fractionation system's geometry can be selected to optimize separation on the basis of size, and that exponential sensitivity should be the norm. Separation on the basis of other characteristics can be optimized by a similar line of reasoning, although exponential sensitivity should not be expected in the general case.

Equation (11) further provides insights into the possibility of applying optical fractionation to such objects as proteins and nanoclusters whose dimensions a are measured in tens of nanometers. In particular, Eq. (11) demonstrates that moving from 1 micrometer-scale objects to 10 nanometer-scale objects at a fixed angle θ will require enhancing the ratio A/B by several orders of magnitude. This can, in principle, be accomplished by increasing the intensity of the light, reducing its wavelength, and selecting a wavelength for which the interaction with the particles is resonantly enhanced.

Implementing optical fractionation in such a system involves creating an array of traps that spans the input mixed flow in such a way that the desired fraction of particles is deflected across the separatrix and into the buffer flow. In one aspect, successful operation requires that the sample have low enough diffusivity or motility that the undesired fraction spontaneously crosses the separatrix at an acceptably low rate.

However, another aspect of the present invention is directed to the opposite case, where the desired fraction is more diffusive or motile than the undesired fraction. In addition, it can further be directed to the case where the desired fraction interacts less strongly than the other fraction, and so would not be selected by conventional optical fractionation. The greatest benefits from the present invention would be realized in systems for which both conditions apply, although either is sufficient.

FIG. 1 depicts a microfluidic H-junction 100 with two fluid flows. One flow, the mixed input flow 110, contains the heterogeneous sample to be fractionated. The other flow, the buffer flow 120, is composed of the background, or buffer fluid. Objects in the input flow 110 encounter an array of optical tweezers 130, arranged at an angle θ with respect to the flow, which deflects the selected fraction of the sample into the buffer output flow 140 for collection. The undeflected fraction of the sample remains in the original stream, or output flow 150, where it is collected.

Figure 2:
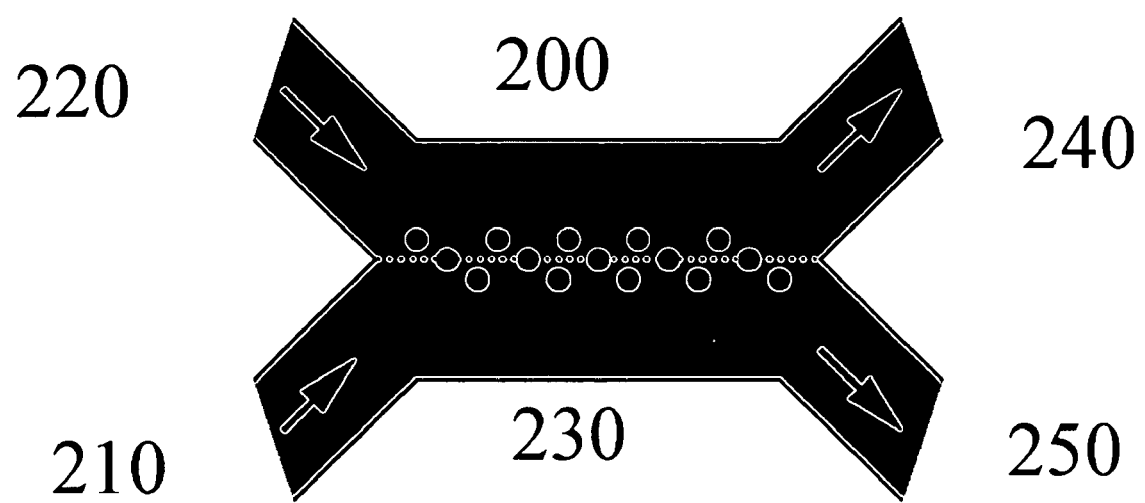
FIG. 2 shows reverse optical fractionation wherein a microfluidic H-junction contains two flowing fluids, one of which contains a heterogeneous sample to be fractionated, and the other of which contains only buffer solution.
Figure 3:
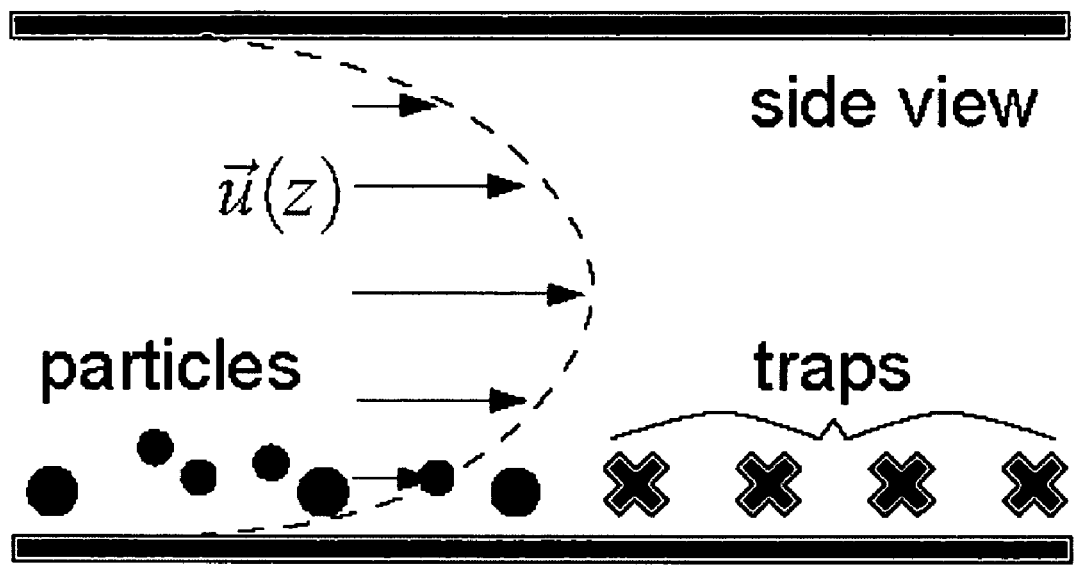
FIG. 3A shows a side view of a schematic for optical fractionation.
FIG. 3B shows a top view of the optical fractionation in 3A.
Figure 3:
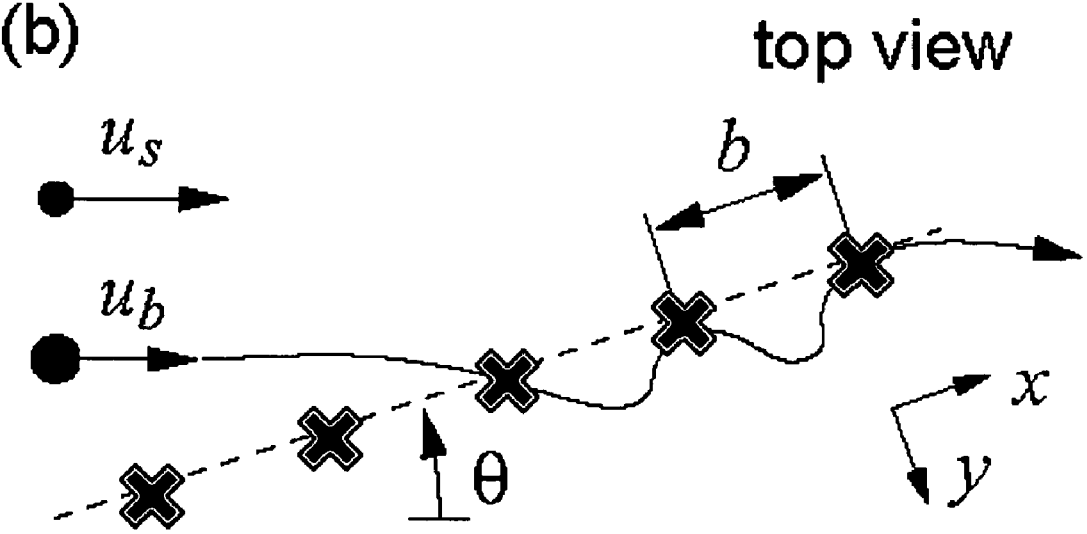

As shown in FIG. 2 rather than creating optical trap arrays to direct objects out of the mixed input flow 110 and into the buffer flow 120, the invention can also use optical traps to direct objects back into the input mixed flow as they attempt to cross the separatrix, either by diffusion or by actively swimming. As in the conventional method shown in FIG. 1, a microfluidic H-junction 200 contains two flowing fluid streams, one of which 210 contains a heterogenous sample to be fractionated, and the other 220 of which contains only buffer solution. Only those objects in the mixed input flow 210 that attempt to cross the separtrix between the two flows encounter an array of optical traps 230 arrangd so as to direct objects back into the mixed input flow 210. Objects which cross the separatrix through the array of traps 230 are collected in the buffer output flow 240. Those that remain in the original input flow, either because they are less diffusive or because they were deflected by the array of traps 230, are collected separately in the output flow 250. In this case, the less diffusive or motile objects will be deflected back into the mixed input flow, while the more mobile fraction will escape the traps and cross the separatrix to be collected. Similarly, objects that are less strongly influenced by the optical traps will be more able to cross the separatrix to be collected.

Whereas optical fractionation requires a large enough number of optical traps to fill the entire mixed input flow, this reversed process requires only enough traps to cover a region just around the separatrix between the flows. Consequently, reverse optical fractionation requires far fewer optical traps than conventional optical fractionation and so makes more efficient use of the laser light required to create the traps.

To the extent that optical fractionation has well-documented advantages over other sorting techniques, reverse optical fractionation offers the same advantages. These include continuous operation rather than batch-mode operation, continuous optimization through adjustment of: laser power, laser wavelength, optical tweezer geometry, driving force, and exponential sensitivity to size. Reverse optical fractionation extends these advantages to systems for which conventional optical fractionation is either inapplicable or impractical. As with conventional optical fractionation, reverse optical fractionation may beneficially take advantage of the polarization of the trapping light or the mode structure of the trapping beams to sort objects on the basis of their birefringence, optical activity, elasticity, as well as such properties as size, optical scattering cross-section, optical absorptivity, surface charge, and shape.

Microfluidic H-junctions are known to be useful for sorting objects on the basis of their diffusivity. The addition of optical tweezer arrays organized for reverse optical fractionation greatly enhances the selectivity of the process, and offers a vast array of new physical bases by which to sort objects.

Figure 6:
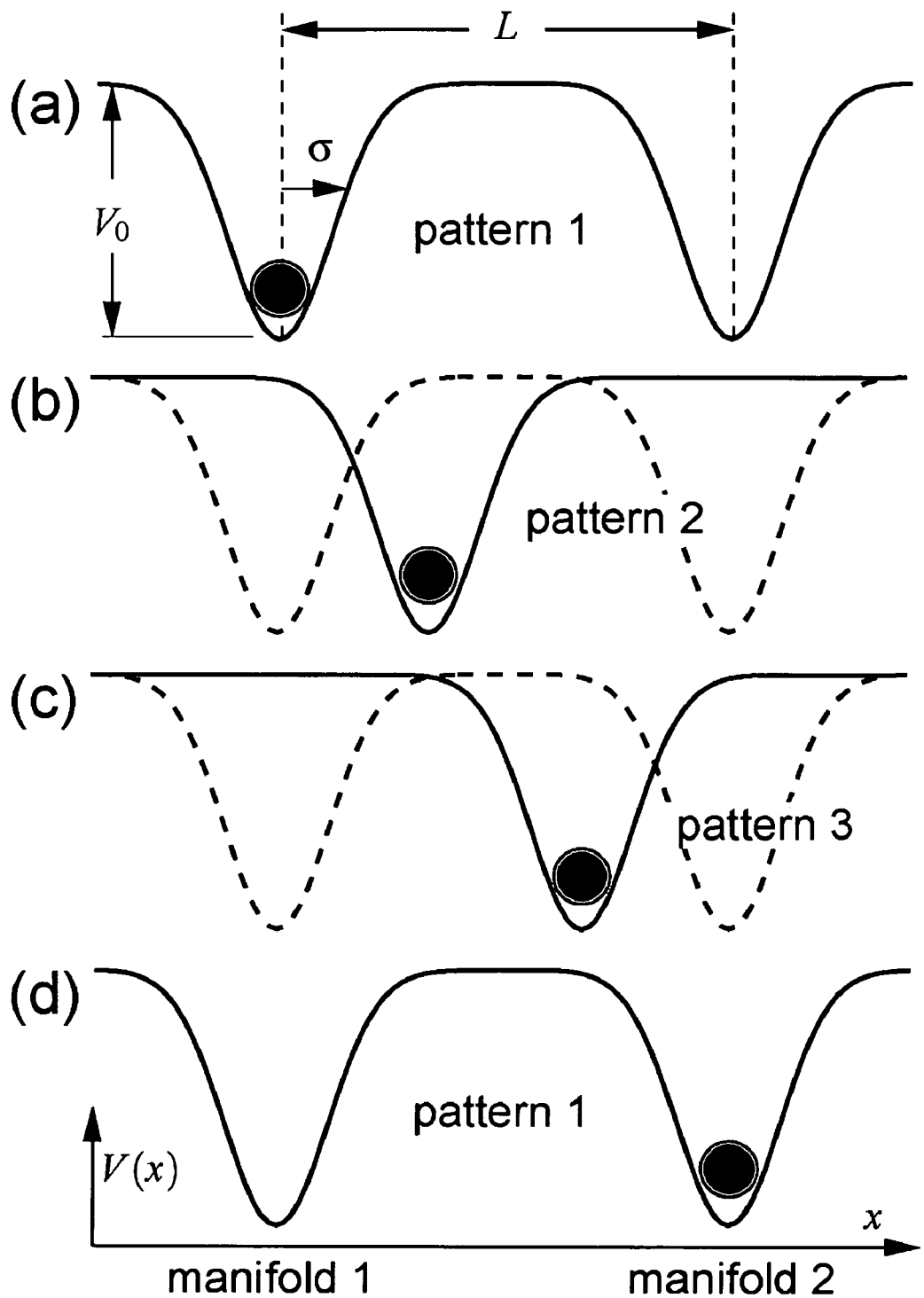
FIG. 6A illustrates a prior art optical peristalsis method wherein a pattern of optical traps localize an object.
FIG. 6B illustrates replacement of an optical trap pattern with another shifted by a distance.
FIG. 6C illustrates yet another shifted pattern of traps.
FIG. 6D illustrates completion of one cycle of optical peristalsis.

In another aspect of the present invention, thermal ratcheting is utilized. FIGS. 6(A–D) show the principal upon which optical peristalsis operates and will be useful for explaining the features of the optical thermal ratchet. In FIG. 6A, a pattern of discrete optical traps is shown localizing a single object. The pattern is schematically represented as two discrete potential energy wells, each of width a, separated by distance L. In practice, an actual pattern would include a great many optical traps organized into manifolds. The goal of both optical peristalsis and also of the herein disclosed optical thermal ratchet methodology is to transfer objects from one manifold of traps to another. The two approaches differ in how they accomplish this.

In optical peristalsis, the initial pattern of traps is replaced with another in which the manifolds are shifted by a distance comparable to a, (see FIG. 6B). Because the new potential wells overlap with the old, particles are transferred deterministically to the nearest manifolds on the new pattern. This process repeats in FIG. 6C with yet another shifted pattern of traps. One cycle of optical peristalsis is complete when the original pattern is projected, (see FIG. 6)). The net effect of this cycle is to transfer the trapped particle from one manifold of traps in the first pattern to the next manifold, also in the first pattern. In practice a great many particles can be trapped in a great many optical traps; and all would be transferred forward by one set of manifolds in each optical peristalsis cycle. The direction of motion is unambiguously determined by the sequence's order and can be reversed only by reversing that order.

The optical thermal ratchet differs from optical peristalsis in that the separation between manifolds in the direction of motion is substantially larger than the individual traps' widths. Consequently, particles trapped in the first pattern are left free to diffuse when the second pattern is energized. Those particles that diffuse far enough to reach the nearest manifold in the second pattern rapidly become localized. This localized fraction then can be transferred forward (again by diffusion) once the third pattern is projected, and again be transferred when the cycle returns to the first pattern. Unlike optical peristalsis, in which deterministic transport ensures that all trapped objects move forward in each cycle, this biased diffusion will transport only a fraction of the sample forward.

This embodiment of thermal ratchets, however, leads to a new opportunity. Particles too slow to catch the forward-going waves might still diffuse far enough to catch a well retrograde to their starting point when the third pattern of FIG. 6C is illuminated. These particles would be transferred backward by one third of the inter-manifold separation at each cycle. Whether a population travels forward or backward through the sequence of trapping patterns is determined by a balance between the particles' diffusion rates and the rate at which the sequence cycles. Changing the cycling rate therefore can change the direction of mean motion, a phenomenon known as flux reversal.

The expected flux of particles under the influence of cycling optical tweezer patterns can be calculated. A tweezer at position $x_j$ may be modeled as a Gaussian potential well.

$$u_j(x) = -V_0 \exp\left(-\frac{(x-x_j)^2}{2\sigma^2}\right) \quad (12)$$

This well has a depth $V_o$ and width $\sigma$. This potential well is manifestly spatially symmetric. A pattern of wells establishes one state of the three-state cycle required for ratchet behavior. As an illustrative example, the wells can be considered in a pattern to be equally spaced by a distance L, so that the overall potential in state k is $$V_k(x) = -\sum_{i=-N}^{N} -V_0 \exp\left(-\frac{\left(x-jL-k\frac{L}{3}\right)^2}{2\sigma^2}\right) \quad (13)$$

where k=0, 1, or 2. Again, as an illustrative example, the potential energy landscape can be considered to cycle repeatedly through these three states at even intervals T. This time is to be compared with the time $$\tau = \frac{L^2}{2D} \quad (14)$$

required for particles of diffusivity D to diffuse through the system. The balance between T and τ turns out to determine which direction a particle is driven through the system by the sequence of potential energy states.

The probability p(x,t)dx to find a Brownian particle with dx of position x at time t under the combined influence of the optical traps and random thermal forces is governed by the master equation:

$$p(y,t+\tau)=\int P(y,\tau|x,0)p(x,t)dx \quad (15)$$

where the propagator for each state k is given by, $$P_k(y,t|x,0)=e^L \quad (16)$$

for times t<T, with:

$$L(y) = D\left(\frac{\partial^2}{\partial y^2} - \beta \frac{\partial^2 V(y)}{\partial y^2}\right) \quad (17)$$

and where $\beta^{-1}$ is the thermal energy scale. The master equation for one complete three-state cycle is, $$p(y,t+3T)=\int dy_3 P_3(y_3,T|y_2,0)\int dy_2 P_2(y_2,T|y_1,0)\int dy_1 P_1(y_1,T|x,0)p(x,t) \quad (18)$$

For the symmetric optical tweezer potentials we are considering, this master equation has a steady-state solution such that:

$$p(x,t+3T)=p(x,t) \quad (19)$$

The mean velocity of this steady-state then is given by:

$$v = -\int p(x) \frac{\partial V_3(x)}{\partial x} + \frac{\partial p(x)}{\partial x} dx \quad (20)$$

Figure 7:
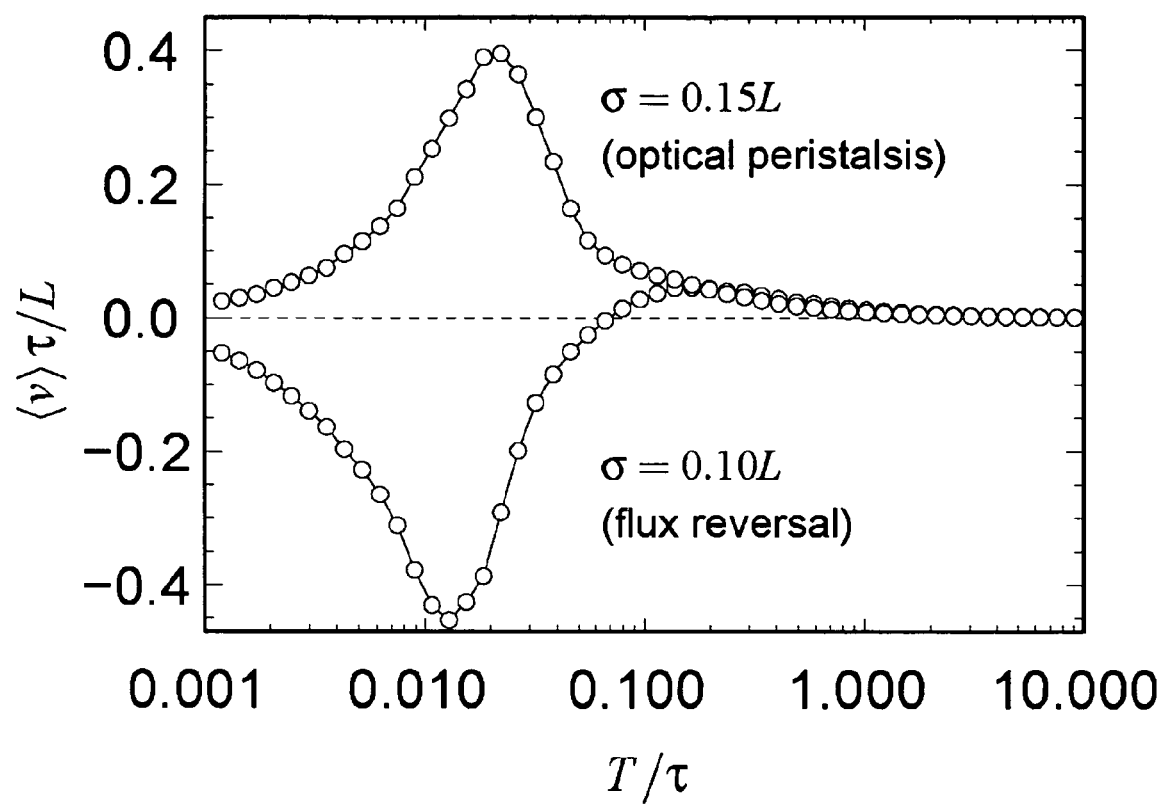
FIG. 7 illustrates numerical solution of equations of motion for an optical thermal ratchet implementation demonstrating flux reversal.

FIG. 7 shows numerical solutions of this system of equations for $\beta V_o=10$ and two representative values of σ/L. For very small values of the cycle time T, particles are unable to keep up with the rapidly evolving potential energy landscape, and so diffuse randomly; the mean velocity consequently vanishes in this limit. If traps in consecutive patterns overlap (σ=0.15 L shown in FIG. 7) particles pass deterministically from trap to trap, yielding a uniformly positive drift velocity. This transfer reaches it maximum efficiency for moderate cycle times T, and does not improve for longer dwell times. Consequently, the drift velocity falls off as 1/T in the long-time limit.

More widely separate traps ($\sigma$=0.10 L, in FIG. 7) yield another behavior. Here, particles are able to keep up with the forward-going wave for sufficiently large values of T. Faster cycling, however, leads to flux reversal, characterized by negative values of v. This numerical result demonstrates the principle by which arrays of optical tweezers can be used to implement a fully symmetric thermal ratchet with flux reversal.

As shown in FIG. 7, crossover occurs from deterministic optical peristalsis at $\sigma$=0.15 L to thermal ratchet behavior with flux reversal at $\sigma$=0.10 L for a three-state cycle of Gaussian well potentials at $\beta V_o$=10.

To this point, flux reversal has been described as resulting from variation in the cycle time, T. The same effect can arise for different populations in a heterogeneous sample whose differing diffusion coefficients yield different values of $\tau$. These different populations might be induced to move simultaneously in opposite directions provided that T is selected to drive one population forward and the other backward. In this way, the described optical thermal ratchet is useful for separating and purifying small fluid-borne objects.

A preferred optical approach to implementing a reversible thermal ratchet has advantages over other ratchet-based separation schemes. For example, thermal ratchets based on interdigitated electrode arrays have been applied to sorting DNA fragments. These, however, require sophisticated microfabrication, whereas the optical ratchet can be implemented inexpensively and readily integrated into microfluidic devices for lab-on-a-chip applications. An optical ratchet based on a single time-shared scanned optical tweezer previously has been demonstrated to induce flux reversal. This approach relies on creating a spatially asymmetric potential energy landscape in a time-averaged sense, and thus the system operates on a different principle from the process described above. In the preferred system described herein, each optical trap in each pattern provides a spatially symmetric potential energy well; and the patterns themselves are spatially symmetric. Unidirectional transport is driven by breaking spatiotemporal symmetry through a sequence of at least three patterns in each cycle.

One of the previously proposed symmetric thermal ratchet examples also involves a sequences of three states. This approach relied on particles being allowed to diffuse only in one state, however, with the other two acting as a deterministic ratchet and thereby biasing the diffusion. The process described in this document involves both diffusion and localization in all three states, and therefore offers more selectivity and more rapid sorting of heterogeneous samples.

While preferred embodiments have been illustrated and described, it should be understood that changes and modifications can be made therein in accordance with one of ordinary skill in the art without departing from the invention in its broader aspects. Various features of the invention are defined in the following claims.

I claim:

1. An apparatus for sorting populations of small objects, comprising:
   a first channel and a second channel;
   a force source for driving the population of small objects through the channels;
   a plurality of manifolds located at a convergence of the first channel and the second channel and comprising beams of laser light for forming a plurality of optical traps;
   the optical traps being organized into a plurality of patterns wherein the patterns are arranged such that the manifolds of one pattern are separated by the manifolds of the remaining patterns; and
   the optical traps being oriented at an angle with respect to the driving force and arranged such that each pattern of optical traps is separated by the others;
   wherein the population of small objects are sorted into at least one desired fraction and an undesired fraction.

2. The apparatus of claim 1, wherein the population of small objects is dispersed in a fluid medium disposed in the first channel and wherein a buffer is disposed in the second channel.

3. The apparatus of claim 1, wherein the channels comprise an H-junction.

4. The apparatus of claim 1, wherein the optical traps are created by holographic optical means.

5. The apparatus of claim 1, wherein the undesired fraction is more diffusive or motile than the desired fraction.

6. The apparatus of claim 1, wherein the desired fraction is more diffusive or motile than the undesired fraction.

7. The apparatus of claim 1, wherein the separation between the manifolds in the direction of the driving force is substantially larger than the individual traps widths.

8. The apparatus of claim 7, wherein the optical traps are adapted to move forward only a portion of the population of small particles as the patterns are sequentially energized.

9. The apparatus of claim 7, wherein the patterns are adapted to allow the population of small particles trapped in one pattern to diffuse when another pattern are energized.

10. A method of continuously separating populations of small particles, comprising the steps of:
    providing an external force to drive the population of small particles;
    focusing beams of laser light to form a plurality of optical traps; and
    providing a plurality of patterns each comprising at least one manifold, each manifold including at least one trap; and
    thermally energizing each pattern at intervals wherein the particles trapped in a previously thermally energized pattern are free to diffuse when another pattern is thermally energized;
    wherein the population of small objects are sorted into at least one desired fraction and an undesired fraction.

11. The method of claim 10, further comprising creating the optical traps by holographic optical tweezer technique.

12. The method of claim 10, wherein the separation between the manifolds in the direction of the driving force is substantially larger than the individual traps widths.

13. The method of claim 10, wherein only a fraction of the population of small particles moves forward through the optical traps as the patterns are sequentially energized.

14. The method of claim 10, wherein the population of small particles trapped in one pattern are left free to diffuse when another pattern is energized.

15. The method of claim 10, wherein some of the particles move forward through the optical trap array and some of the particles move backward through the patterns.

* * * * *